(12) United States Patent
Minamikawa et al.

(10) Patent No.: US 8,039,022 B2
(45) Date of Patent: Oct. 18, 2011

(54) AQUEOUS HYDROGEN PEROXIDE FOR STERILIZATION

(75) Inventors: Yoshitsugu Minamikawa, Mie (JP); Morinari Matsuura, Mie (JP); Masamichi Hattori, Mie (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/914,802

(22) PCT Filed: May 16, 2006

(86) PCT No.: PCT/JP2006/309709
§ 371 (c)(1), (2), (4) Date: Dec. 16, 2008

(87) PCT Pub. No.: WO2006/123636
PCT Pub. Date: Nov. 23, 2006

(65) Prior Publication Data
US 2009/0175760 A1    Jul. 9, 2009

(30) Foreign Application Priority Data
May 19, 2005  (JP) ................................. 2005-147255

(51) Int. Cl.
*A01N 59/00*    (2006.01)
(52) U.S. Cl. ........................... 424/616; 424/601; 422/28
(58) Field of Classification Search .................... 422/28, 422/292, 302; 424/601, 616
See application file for complete search history.

(56) References Cited

U.S. PATENT DOCUMENTS

| | | | | |
|---|---|---|---|---|
| 2,871,103 A | * | 1/1959 | Skinner et al. ................. | 423/591 |
| 4,166,807 A | | 9/1979 | Komatsu et al. | |
| 4,226,636 A | | 10/1980 | Mizutani et al. | |
| 4,518,585 A | * | 5/1985 | Greene et al. ................. | 424/616 |
| 5,944,912 A | * | 8/1999 | Jenkins et al. .................. | 134/40 |
| 7,270,499 B2 | * | 9/2007 | Greenberg ................ | 405/128.5 |
| 2002/0159915 A1 | * | 10/2002 | Zelina et al. ...................... | 422/3 |

FOREIGN PATENT DOCUMENTS

| | | |
|---|---|---|
| EP | 0 527 228 A1 | 2/1993 |
| FR | 2.022.713 | 8/1970 |
| GB | 1289156 | 9/1972 |
| JP | 10-258811 | 9/1998 |
| JP | 11-035306 | 2/1999 |

OTHER PUBLICATIONS

English language machine translation of JP 11-035306, inventor: Y. Nishimura.*
Supplementary European Search Report for Application No. 02775302.9-1213 PCT/JP0210434, dated Feb. 21, 2008.
Anonymous, "Florite" (Calcium silicate), Internet Article, www.tokuyama.co.jp/eng/products/chem/si/florite.html (XP002466634), retrieved Jan. 23, 2008.
Chinese Official Action issued Mar. 27, 2009, for Application No. 200680017168.7 (English translation only).

* cited by examiner

*Primary Examiner* — Sean E Conley
(74) *Attorney, Agent, or Firm* — Antonelli, Terry, Stout & Kraus, LLP.

(57) ABSTRACT

The present invention provides a hydrogen peroxide solution for sterilization which has a hydrogen peroxide concentration of 30 to 45% by weight, an Fe concentration of 2 ppb or less and an Al concentration of at least 15 ppb and in which a concentration of a stabilizer comprising orthophosphoric acid is 40 ppm at the most. The above hydrogen peroxide solution for sterilization is used for sterilizing vessels filled with beverages and foods and packaging materials in an aseptic filling equipment. The above hydrogen peroxide solution for sterilization has less evaporation residue, does not clog a narrow piping part such as a spray nozzle and therefore makes it possible to stably operate an aseptic filling equipment. Further, an austenite base stainless material can be used as a material for the transporting facilities and the tanks.

7 Claims, No Drawings

AQUEOUS HYDROGEN PEROXIDE FOR STERILIZATION

BACKGROUND OF THE INVENTION

The present invention relates to a hydrogen peroxide solution for sterilization which is heated and evaporated and in which hydrogen peroxide evaporated is used as a bactericide. More specifically, it relates to a hydrogen peroxide solution for sterilization which contains less amount of a stabilizer added to the hydrogen peroxide solution and is reduced in an amount of impurities to the utmost and which contains a specific additive component.

RELATED ART

In recent years, according to development of equipments in which beverages, foods and the like are aseptically filled into vessels and popularization of PET bottles, bactericides used for aseptic tilling which are excellent in handling have come to be desired. A method in which a hydrogen peroxide solution is evaporated by heating to a boiling point thereof or higher in an evaporator and in which a gas of hydrogen peroxide is sprayed together with air to sterilize a vessel is known as a sterilizing method using a hydrogen peroxide solution (refer to a patent document 1). However, involved therein are the problems that a part of a stabilizer added to a hydrogen peroxide solution is adhered and remains onto a spray nozzle and an evaporator to clog a narrow piping part and that stable operation of an aseptic filling equipment is disturbed.

Stabilizers are added to a hydrogen peroxide solution used for industrial uses and food additives in order to inhibit the hydrogen peroxide solution from being decomposed by decomposing components contained therein. Substances having an ability to form a coordinate compound or a chelate compound with decomposing components, for example, Fe are used for a stabilizer, and a method in which pyrophosphoric acid salts are used in combination with inorganic compounds such as orthophosphoric acid has so far been known. Known is a method in which an amount of substances adhered onto a spray nozzle and an evaporator is reduced by controlling the addition amounts of the above compounds (refer to a patent document 2). However, involved therein is the problem that an inhibition in an amount of a stabilizer leads to an increase in risks such as loss of hydrogen peroxide by decomposition and abnormal decomposition thereof in transportation and storage in tanks. Further, involved therein is the problem that an austenite base stainless material used for parts such as a nozzle, a filling unit and the like which are brought into contact with a hydrogen peroxide solution is reacted with a stabilizer having an ability to form a chelate compound and results in eluting Fe, Cr and the like to increase decomposition of hydrogen peroxide.

A semiconductor grade hydrogen peroxide solution scarcely contains hydrogen peroxide decomposing components, and a stabilizer is not added thereto. Accordingly, solved is the problem that the stabilizer is adhered and remains onto a spray nozzle and an evaporator and clogs a narrow piping part to disturb stable operation of an aseptic filling equipment. However, the semiconductor grade hydrogen peroxide solution is required to use high grade materials for delivering, transporting and receiving facilities and the like, and sufficient attentions and high costs are required for handling it.

Patent document 1: Japanese Patent Application Laid-Open No. 47242/1999
Patent document 2: Japanese Patent Application Laid-Open No. 152116/1998

DISCLOSURE OF THE INVENTION

An object of the present invention is to provide a hydrogen peroxide solution for sterilization which solves the foregoing problems in conventional techniques and enables stable operation of an aseptic filling equipment and which can stably be transported and stored even in transporting facilities and tanks made by using an austenite base stainless material.

Intensive researches repeated by the present inventors on relation among an amount of a stabilizer added to a hydrogen peroxide solution, the kind of the stabilizer, an evaporation residue, impurities contained, stability and the like have resulted in finding that use of a hydrogen peroxide solution which has an Fe concentration of 2 ppb or less and an Al concentration of at least 15 ppb and to which orthophosphoric acid is added as a stabilizer so that a whole addition amount thereof is 40 ppm at the maximum makes it possible to reduce an amount thereof which is adhered and remains onto a spray nozzle and an evaporator and stably operate an aseptic filling equipment without clogging a narrow piping part. Further, they have found that in the above hydrogen peroxide solution, hydrogen peroxide is scarcely decomposed during transportation and storage even in transporting facilities and tanks made by using an austenite base stainless material. The present inventors have reached the present invention based on the above knowledges.

That is, the present invention relates to a hydrogen peroxide solution for sterilization which is used in an aseptic filling equipment and which sterilizes a vessel or a packaging material by hydrogen peroxide vapor, wherein a hydrogen peroxide concentration is 30 to 45% by weight; an Fe concentration is 2 ppb or less; an Al concentration is at least 15 ppb; and a concentration of a stabilizer comprising at least orthophosphoric acid is 40 ppm at the most. Further, the present invention relates to a sterilizing method for a vessel or a packaging material using an aseptic filling equipment, comprising a step in which the above hydrogen peroxide solution for sterilization is heated and evaporated and in which resulting hydrogen peroxide vapor is brought into contact with the above vessel or packaging material.

BEST MODE FOR CARRYING OUT THE INVENTION

In the present invention, a hydrogen peroxide solution which is not a semiconductor grade can be used. The hydrogen peroxide solution of the present invention for sterilization has a hydrogen peroxide concentration of 30 to 45% by weight. In the present invention, a stabilizer (sodium pyrophosphate and orthophosphoric acid) in which a safety and an effectiveness are confirmed and which is designated as an additive for foods by Minister of Health, Labor and Welfare is preferably added to the hydrogen peroxide solution, and only orthophosphoric acid is particularly preferably added as the stabilizer.

An addition amount of the stabilizer is preferably as small as possible, and considering inactivation of hydrogen peroxide decomposing components contained in a general purpose hydrogen peroxide solution and clogging of a narrow piping part, it is 40 ppm at the most, preferably 1 to 40 ppm. If it exceeds 40 ppm, a spray nozzle for spraying vaporized hydrogen peroxide onto a vessel or a packaging material is frequently clogged by the stabilizer contained in the hydrogen peroxide solution for sterilization, and a removing work for adhered matters is required, which results in disturbing stable operation of an aseptic filling equipment. On the other hand, if the stabilizer is not added, a stability of hydrogen peroxide is deteriorated to bring about abnormal decomposition, and a problem on the safety is caused. In the present application, %, ppm and ppb are based on a weight in all cases.

Heavy metals are known as decomposing components for a hydrogen peroxide solution, and decomposing components contained in a hydrogen peroxide solution which is industrially produced are limited almost to Fe, Cr, Ni and Pd. In the hydrogen peroxide solution of the present invention for sterilization, the concentrations of Ni and Pd each are controlled preferably to 0.1 ppb or less, more preferably 0.01 to 0.1 ppb. Further, the concentrations of Fe and Cr each are controlled preferably to 2 ppb or less, more preferably 0.1 to 2 ppb. In the present invention, the Fe concentration is controlled particularly preferably to 2 ppb or less. A method for controlling the Fe concentration to 2 ppb or less includes a method in which the hydrogen peroxide solution is brought into contact with a cation exchange resin or an anion exchange resin and a method in which the hydrogen peroxide solution is heated and vaporized to condense and refine hydrogen peroxide-containing steam.

In the hydrogen peroxide solution of the present invention for sterilization, an Al concentration is at least 15 ppb, preferably 15 to 1000 ppb, more preferably 15 to 300 ppb and further preferably 15 to 200 ppb. A method for controlling the Al concentration to at least 15 ppb includes a method in which the hydrogen peroxide solution is brought into contact with a cation exchange resin or an anion exchange resin and a method in which the hydrogen peroxide solution is heated and vaporized to condense and refine hydrogen peroxide-containing steam.

The hydrogen peroxide solution of the present invention for sterilization is used particularly preferably for sterilizing vessels and packaging materials in aseptic filling of beverages, foods and the like. A sterilizing unit constituting a part of an aseptic filling equipment comprises at least a hydrogen peroxide-supplying part, an evaporator equipped with a heating device and a spray nozzle. The structure thereof shall not specifically be restricted, and publicly known equipments, for example, the equipments described in the patent documents 1 and 2 described above can be used.

The hydrogen peroxide solution for sterilization which has been introduced from the hydrogen peroxide-supplying part into the evaporator is vaporized by heating at a temperature of a boiling point thereof or higher, preferably the boiling point to 200° C. by the heating device. The vaporized hydrogen peroxide solution for sterilization moves to a downstream side in the evaporator by compressed air introduced from the hydrogen peroxide-supplying part or a supplying part which is independent from this, and it is sprayed onto a vessel or a packaging material from the spray nozzle disposed at an end of a downstream side in the evaporator. The gaseous hydrogen peroxide solution sprayed is cooled and condensed to be turned into mists, and they are adhered on the surface of the vessel or the packaging material in the form of fine droplets to exhibit a bactericidal action. The vessel or the packaging material subjected to bactericidal treatment is dried and sent to an aseptic filling step for beverages, foods and the like.

The hydrogen peroxide solution of the present invention for sterilization contains Al and orthophosphoric acid. Al and orthophosphoric acid have a function to form a passive coating film of aluminum phosphate on the surface of an austenite base stainless material and reduce elution of Fe, Cr and Ni to thereby inhibit hydrogen peroxide from being decomposed. Accordingly, the austenite base stainless material such as SUS304, 304L, 316 and 316L is preferably used as a material for parts in the stabilizing unit which are brought into contact with the above hydrogen peroxide solution for sterilization.

EXAMPLES

Next, the present invention shall be explained in further details with reference to examples and comparative examples.

However, the present invention shall not be restricted by the following examples. The Al concentrations, the Fe concentrations and the Cr concentrations were measured by atomic absorption analysis, and the others were measured according to JIS K-1463.
(1) Hydrogen Peroxide Concentration
Determined by titrating with an N/10 potassium permanganate aqueous solution.
(2) Stability
A fixed amount of the sample was heated in a boiling water bath for 5 hours. After cooling down, water was added thereto to adjust the volume to that before heating, and then hydrogen peroxide was immediately determined to calculate the stability (%) according to the following equation:

$$H = (J'/J) \times 100$$

(wherein H is the stability (%); J' is the hydrogen peroxide concentration after heated for 5 hours; and J is the hydrogen peroxide concentration before heated).
(3) Al Concentration
Measured by atomic absorption analysis.
(4) Fe Concentration
Measured by atomic absorption analysis.
(5) Cr Concentration
Measured by atomic absorption analysis
(6) Evaporation Residue
The sample 250 g was taken in a beaker, and a platinum piece was put therein to decompose hydrogen peroxide. Thereafter, the decomposed solution was transferred into a platinum dish and evaporated and dried up on a water bath, and then the residue was dried at 105 to 110° C. for 2 hours. After left cooling in a desiccator containing silica gel, a weight of the residue was measured to calculate the evaporation residue (ppm) according to the following equation:

$$C = (D/S) \times 10^6$$

(wherein C is the evaporation residue (ppm); D is an amount (g) of the residue; and S is an amount (g) of the sample taken.

Examples 1 to 2 and Comparative Examples 1 to 4

A hydrogen peroxide concentration of the prescribed hydrogen peroxide solution was adjusted to about 35% by weight. A prescribed amount of the stabilizer was added thereto to obtain the respective sample hydrogen peroxide solutions, and the respective items thereof were measured. The results thereof are shown in Table 1.

TABLE 1

| | Addition amount of stabilizer | | Measurement results | | | | | |
|---|---|---|---|---|---|---|---|---|
| | 85% $H_3PO_4$ ppm | $Na_4P_2O_7 \cdot 10 H_2O$ ppm | $H_2O_2$ % | Stability % | Al ppb | Fe ppb | Cr ppb | Evaporation residue ppm |
| Example 1 | 8 | 0 | 35.29 | 98.72 | 17 | 1 | <1 | 7 |
| Example 2 | 21 | 0 | 35.29 | 99.12 | 19 | 1 | <1 | 18 |
| Comparative Example 1 | 6 | 4 | 35.29 | 99.74 | 19 | 1 | <1 | 7 |
| Comparative Example 2 | 15 | 10 | 35.29 | 99.85 | 15 | 1 | <1 | 20 |
| Comparative Example 3 | 30 | 19 | 35.30 | 99.85 | 16 | 1 | <1 | 39 |
| Comparative Example 4 | 0 | 0 | 35.29 | 97.34 | 20 | 1 | <1 | <1 |

Next, the respective samples 330 g were taken in a polyethylene vessel having a volume of 1 L, and a SUS304L piece (pre-treatment: washing for degreasing→dipping in 30% nitric acid for 3 hours→washing with water→air drying, size: 30×40×4 mm, surface area: 0.00296 m²) was put therein and stored at room temperature while dipping. During the storage, only the hydrogen peroxide solution was exchanged with new one after 7 days and 14 days passed since starting dipping. The hydrogen peroxide solutions taken out after 21 days passed were used to measure the same items as described above. The results thereof are shown in Table 2.

TABLE 2

| | Measurement results | | | | | |
|---|---|---|---|---|---|---|
| | $H_2O_2$ % | Stability % | Al ppb | Fe ppb | Cr ppb | Evaporation residue ppm |
| Example 1 | 35.24 | 85.24 | 18 | 4 | 1 | 7 |
| Example 2 | 35.27 | 85.45 | 17 | 5 | 1 | 19 |
| Comparative Example 1 | 35.25 | 69.90 | 20 | 65 | 16 | 6 |
| Comparative Example 2 | 35.27 | 88.99 | 19 | 59 | 15 | 20 |
| Comparative Example 3 | 35.26 | 91.80 | 20 | 92 | 21 | 40 |
| Comparative Example 4 | 34.91 | 78.68 | 17 | 6 | 1 | <1 |

Examples 3 to 6 and Comparative Examples 5 to 6

A hydrogen peroxide concentration of the prescribed hydrogen peroxide solution was controlled to about 35% by weight. The prescribed amounts of the stabilizer and aluminum nitrate were added thereto to prepare the respective sample hydrogen peroxide solutions, and the respective items thereof were measured. The results thereof are shown in Table 3.

TABLE 3

| | Aluminum nitrate (reduced to Al atom) ppb | 85% $H_3PO_4$ ppm | $H_2O_2$ % | Stability % | Al ppb | Fe ppb | Cr ppb |
|---|---|---|---|---|---|---|---|
| Comparative Example 5 | 0 | 2 | 35.25 | 99.94 | <1 | <1 | <1 |
| Comparative Example 6 | 0 | 5 | 35.24 | 99.91 | <1 | <1 | <1 |
| Example 3 | 50 | 2 | 35.23 | 99.91 | 60 | <1 | <1 |
| Example 4 | 50 | 5 | 35.21 | 99.97 | 56 | <1 | <1 |
| Example 5 | 100 | 2 | 35.21 | 99.88 | 116 | <1 | <1 |
| Example 6 | 100 | 5 | 35.20 | 99.97 | 109 | <1 | <1 |

The respective samples 330 g were taken in a polyethylene vessel having a volume of 1 L, and a SUS304L piece (pre-treatment: washing for degreasing→dipping in 30% nitric acid for 3 hours→washing with water→air drying, size: 30×40×4 mm, surface area: 0.00296 m²) was put therein and stored at room temperature while dipping. During the storage, only the hydrogen peroxide solution was exchanged with new one after 7 days and 14 days passed since starting dipping. The hydrogen peroxide solutions taken out after 21 days passed were used to measure the same items as described above. The results thereof are shown in Table 4.

TABLE 4

| | $H_2O_2$ % | Stability % | Al ppb | Fe ppb | Cr ppb |
|---|---|---|---|---|---|
| Comparative Example 5 | 35.15 | 88.96 | <1 | 4 | <1 |
| Comparative Example 6 | 34.17 | 89.84 | <1 | 4 | <1 |
| Example 3 | 35.15 | 92.20 | 56 | 3 | <1 |
| Example 4 | 35.18 | 94.05 | 58 | 4 | <1 |
| Example 5 | 35.18 | 99.26 | 117 | 1 | <1 |
| Example 6 | 35.17 | 98.83 | 115 | 3 | <1 |

INDUSTRIAL APPLICABILITY

The present invention makes it possible to stably operate an aseptic filling equipment without allowing a part of stabilizer added to the hydrogen peroxide solution to be adhered and remain onto a spray nozzle and an evaporator to clog a narrow piping part such as a nozzle. Further, if using transporting facilities and tanks made by using an austenite base stainless material, hydrogen peroxide is scarcely decomposed, and therefore the hydrogen peroxide solution can stably be transported and stored.

The invention claimed is:

1. A hydrogen peroxide solution for sterilization which is used in an aseptic filling equipment and which sterilizes a vessel or a packaging material by hydrogen peroxide vapor, said hydrogen peroxide solution comprising hydrogen peroxide, Fe, and Al, wherein a hydrogen peroxide concentration is 30 to 45% by weight; an Fe concentration is 2 ppb or less; and an Al concentration is at least 15 ppb; wherein said solution includes a stabilizer consisting of orthophosphoric acid, and a concentration of the stabilizer consisting of orthophosphoric acid is 40 ppm at the most, wherein the aseptic filling equipment has a spray nozzle and an evaporator, and wherein a material of a part brought into contact with the hydrogen peroxide solution for sterilization is an austenite base stainless material, said hydrogen peroxide solution, containing the Al and the orthophosphoric acid, having a property that the Al and the orthophosphoric acid contained in the hydrogen peroxide solution form a passive coating on said austenite base stainless material.

2. A sterilizing method for a vessel or a packaging material using an aseptic filling equipment having a spray nozzle and an evaporator, comprising a step of heating and evaporating the hydrogen peroxide solution for sterilization as described in claim 1 in the evaporator and in which resulting hydrogen peroxide vapor passes through the spray nozzle and is brought into contact with the vessel or packaging material, and wherein said hydrogen peroxide solution for sterilization comes into contact with a part made of an austenite base stainless material, the Al and the orthophosphoric acid forming a passive coating film on said part made of the austenite base stainless material.

3. The hydrogen peroxide solution as described in claim 1, wherein the concentration of the stabilizer consisting of orthophosphoric acid is 1-40 ppm.

4. The hydrogen peroxide solution as described in claim 1, wherein said solution also includes 0.1 ppb or less of Ni and Pd, and 2 ppb or less of Cr.

5. The hydrogen peroxide solution as described in claim 1, wherein Al is included in the solution in an amount of 15 to 1000 ppb.

6. The hydrogen peroxide solution as described in claim 1, wherein said passive coating on said austenite base stainless material is an aluminum phosphate coating formed from the Al and the orthophosphoric acid of said hydrogen peroxide solution.

7. The sterilizing method according to claim 2, wherein the Al and the orthophosphoric acid form an aluminum phosphate coating on said part made of the austenite base stainless material.

* * * * *